United States Patent
Patel

(10) Patent No.: US 12,427,145 B2
(45) Date of Patent: Sep. 30, 2025

(54) CONTROLLED RELEASE PHARMACEUTICAL COMPOSITION OF SELEXIPAG OR IT'S ACTIVE METABOLITE

(71) Applicant: Jayendrakumar Dasharathlal Patel, Vijapur (IN)

(72) Inventor: Jayendrakumar Dasharathlal Patel, Vijapur (IN)

(73) Assignee: Innovate Therapeutics LLC, Princeton, NJ (US)

( * ) Notice: Subject to any disclaimer, the term of this patent is extended or adjusted under 35 U.S.C. 154(b) by 530 days.

(21) Appl. No.: 17/428,273

(22) PCT Filed: Feb. 2, 2020

(86) PCT No.: PCT/IB2020/050820
§ 371 (c)(1),
(2) Date: Jul. 5, 2022

(87) PCT Pub. No.: WO2020/157730
PCT Pub. Date: Aug. 6, 2020

(65) Prior Publication Data
US 2024/0024311 A1 Jan. 25, 2024

(30) Foreign Application Priority Data
Feb. 3, 2019 (IN) ............................. 201921004220

(51) Int. Cl.
| | |
|---|---|
| A61K 9/00 | (2006.01) |
| A61K 9/20 | (2006.01) |
| A61K 9/28 | (2006.01) |
| A61K 31/4965 | (2006.01) |
| A61P 9/12 | (2006.01) |

(52) U.S. Cl.
CPC ........ *A61K 31/4965* (2013.01); *A61K 9/2009* (2013.01); *A61K 9/2018* (2013.01); *A61K 9/2054* (2013.01); *A61K 9/2077* (2013.01); *A61K 9/2086* (2013.01); *A61K 9/2853* (2013.01); *A61K 9/2866* (2013.01); *A61K 9/2893* (2013.01)

(58) Field of Classification Search
CPC .............. A61K 31/4965; A61K 9/2009; A61K 9/2018; A61K 9/2054; A61K 9/2077; A61K 9/2086; A61K 9/2853; A61K 9/2866; A61K 9/2893; C07D 241/20
See application file for complete search history.

(56) References Cited

U.S. PATENT DOCUMENTS

| | | | |
|---|---|---|---|
| 7,205,302 B2 | 4/2007 | Asaki et al. | |
| 8,394,793 B2 | 3/2013 | Kyoi | |
| 8,629,145 B2 | 1/2014 | Kuwano | |
| 8,889,693 B2 | 11/2014 | Murakami et al. | |
| 9,340,516 B2 | 5/2016 | Itou | |
| RE46,364 E | 4/2017 | Murakami et al. | |
| 10,188,648 B2 | 1/2019 | Villalva et al. | |
| 10,828,298 B2 | 11/2020 | Furuta et al. | |
| 11,382,912 B2 | 7/2022 | Furuta et al. | |
| 2004/0052844 A1 | 3/2004 | Hsiao et al. | |
| 2012/0003307 A1 | 1/2012 | Kashid et al. | |
| 2023/0113077 A1 | 4/2023 | Luyten et al. | |

FOREIGN PATENT DOCUMENTS

| | | | | |
|---|---|---|---|---|
| CN | 107811994 A | * | 3/2018 | ......... A61K 31/4965 |
| JP | 62120315 A | | 6/1987 | |
| JP | 63215620 A | | 9/1988 | |
| JP | 2014009208 A | | 8/2016 | |
| WO | 1998041210 A1 | | 9/1998 | |
| WO | 2002088084 A1 | | 11/2002 | |
| WO | 2005005484 A1 | | 1/2005 | |
| WO | 2007025182 A2 | | 3/2007 | |
| WO | 2009154246 A1 | | 12/2009 | |
| WO | 2009157397 A1 | | 12/2009 | |
| WO | 2010150865 A1 | | 12/2010 | |
| WO | 2017029594 A1 | | 2/2017 | |
| WO | 2017042731 A1 | | 3/2017 | |
| WO | WO-2017109772 A1 | * | 6/2017 | |
| WO | 2017121806 A1 | | 7/2017 | |
| WO | 2018015975 A1 | | 7/2017 | |
| WO | 2018015974 A1 | | 1/2018 | |
| WO | 2018022704 A1 | | 2/2018 | |
| WO | 2021152060 A1 | | 8/2021 | |
| WO | 2021153716 A1 | | 8/2021 | |
| WO | 2022106621 A1 | | 5/2022 | |

OTHER PUBLICATIONS

Satyajit et al. (IJBPAS, Dec. 2018, 7(12): 2038-2055). (Year: 2018).*
Asaki et al. (J. Med. Chem. 2015, 58, 7128-7137) (Year: 2015).*
FDA Prescribing information for selexipag tablets UPTRAVI® ([online] retrieved on Mar. 19, 2025 from: https://www.accessdata.fda.gov/drugsatfda_docs/label/2017/207947s005lbl.pdf, 2017; 22 pages). (Year: 2017).*
Ghosh et al. (Journal of Applied Pharmaceutical Science 01 (02); 2011: 38-49). (Year: 2011).*
English translation of CN 107811994 A; 2018; 7 pages. (Year: 2018).*

(Continued)

*Primary Examiner* — Ernst V Arnold

(57) ABSTRACT

A controlled release pharmaceutical dosage form that improve tolerability by reducing incidence of side effect associated with a Selexipag or its active metabolite contained in the dosage form comprising a release rate controlling ingredient in addition to the Selexipag or its active metabolite that govern a release of the Selexipag or its active metabolite from the dosage form, wherein the dosage form after administration to a mammal in fasting condition providing a. a mean or median Tmax of at least greater than 2 hours for the Selexipag and/or at least greater than 3.5 hours for the active metabolite of the Selexipag, and/or
b. at least 20% lower Cmax for Selexipag and/or it's active metabolite compared to Cmax obtained after administration of the same amount of an immediate release dosage form of Selexipag or its active metabolite in fasting condition.

7 Claims, No Drawings

(56) References Cited

OTHER PUBLICATIONS

C. V. N. Satyajit, M.E. Bhanoji Rao, A Pharmaceutical Formulation and Evaluation of a Cardiovascular Drug for Improving Pulmonary Arterial Hypertension, IJBPAS, Dec. 2018, 7(12): 2038-2055.
Kaufmann P, Okubo K, Bruderer S, Mant T, Yamada T, Dingemanse J, Mukai H. Pharmacokinetics and Tolerability of the Novel Oral Prostacyclin IP Receptor Agonist Selexipag. Am J Cardiovasc Drugs. Jun. 2015; 15(3):195-203. doi: 10.1007/s40256-015-0117-4. PMID: 25850750; PMCID: PMC4452035.
Highlights of Prescribing Information, Uptravi® (selexipag) tablets, for oral use Initial U.S. Approval: 2015.
Medical Review(s), NDA 207947, Uptravi® (selexipag), Center for Drug Evaluation and Research, Application No. 207947Orig1s000.
David B. Badesch et al., "Longterm Survival Among Patients with Scleroderma-associated Pulmonary Arterial Hypertension Treated with Intravenous Epoprostenol," The Journal of Rheumatology, vol. 36, No. 10, pp. 2244-2249, 2009, [online] <www.jrheum.org>, retrieved Mar. 11, 2020.
European Medicines Agency, "Assessment Report, Uptravi, International non-proprietary name: selexipag, Procedure No. EMEA/H/C/003774/0000," 117 pages, Apr. 1, 2016.
G. Bergman et al., "Prostacyclin: Haemodynamic and Metabolic Effects in Patients With Coronary Artery Disease," The Lancet. vol. 317, Issue 8220, pp. 569-572, Mar. 14, 1981, Elsevier B.V.
Hao Yin et al., "Prostaglandin I2 and E2 mediate the protective effects of cyclooxygenase-2 in a mouse model of immune-mediated liver injury," Hepatology, vol. 45, No. 1, pp. 159-169, Jan. 2007.
Irene M. Lang and Sean P. Gaine, "Recent advances in targeting the prostacyclin pathway in pulmonary arterial hypertension," European Respiratory Review, vol. 24, pp. 630-641, 2015.
Marco Idzko et al., "Inhaled iloprost suppresses the cardinal features of asthma via inhibition of airway dendritic cell function," The Journal of Clinical Investigation, Vo. 117, No. 2, pp. 464-472, Feb. 2007, American Society for Clinical Investigation.
Masateru Yamada et al., "Amelioration by beraprost sodium, a prostacyclin analogue, of established renal dysfunction in rat glomerulonephritis model," European Journal of Pharmacology, vol. 449, pp. 167-176, 2002, Elsevier B.V.
P. Henriksson et al., "Prostacyclin infusion in patients with acute myocardial infarction," British Heart Journal, vol. 53, No. 2, pp. 173-179, 1985, [online] <https://heart.bmj.com/>, retrieved Mar. 12, 2020.

\* cited by examiner

CONTROLLED RELEASE PHARMACEUTICAL COMPOSITION OF SELEXIPAG OR IT'S ACTIVE METABOLITE

FIELD OF THE INVENTION

The present invention is relates to a controlled release pharmaceutical composition of Selexipag or its active metabolite having improved tolerability by reduced incident of side effects, to a process for preparing the pharmaceutical composition, and to a method of treating a Pulmonary Arterial Hypertension (PAH) with reduced incident of side effect, comprising administering the controlled release pharmaceutical composition to a mammal, including a human patient, in need of such treatment.

BACKGROUND OF THE INVENTION

Pulmonary Arterial Hypertension (PAH) is a hemodynamic and pathophysiological condition affecting the pulmonary arterioles and characterized by progressive increases in pulmonary vascular resistance and pulmonary artery pressure, ultimately leading to right heart failure and premature death. Recent therapeutic options have significantly improved the long-term outcome of patients with PAH, but PAH remains a disease with a poor prognosis.

Reduced expression of prostacyclin synthases in the lung and reduced levels of prostacyclin are key features of PAH. Prostacyclin is produced by endothelial cells from prostaglandin H2 (PGH2) by the enzyme prostacyclin synthase. Prostacyclin is a potent vasodilator and also has anti-proliferative, antithrombotic, and anti-inflammatory effects. As PAH is associated with vasoconstriction, proliferation, and thrombosis, there is a strong rationale for using prostacyclin treatment. Restoration of IP receptor signalling using prostacyclin receptor (IP receptor) agonists is an effective strategy in the treatment of the disease.

Selexipag, previously also known as NS-304 or ACT-293987, is a potent orally available and highly selective long acting non-prostanoid prostaglandin 12 (PGI-2) receptor agonist, and has been approved in the Europe and in the United State and marketed by Actelion for the treatment of pulmonary arterial hypertension under brand name UPTRAVI®. As a prodrug, it is in vivo transformed by the liver to its active metabolite.

Selexipag and processes for its preparation are disclosed in WO 2002/088084 and U.S. Pat. No. 7,205,302. WO 2010/150865 discloses three crystalline forms of Selexipag, designated form I, form II and form III. It is described that these forms were obtained either in pure form or as binary mixtures. The crystalline forms of WO 2010/150865 are described as useful for the preparation of pharmaceutical formulations and oral dosage forms, such as tablets comprising crystalline Selexipag, are described. WO 2017/121806 discloses an amorphous solid dispersion comprising Selexipag and methods for preparing the same. American Journal of Cardiovascular Drugs, 2015; 15(3): 195-203, discloses Pharmacokinetics and Tolerability of the Novel Oral Prostacyclin IP Receptor Agonist Selexipag.

Selexipag is rapidly absorbed after oral administration and hydrolyzed to the pharmacologically more active metabolite ACT-333679. The ACT-333679 is considered as the major contributor to the overall activity of the drug. A chemical structure of the Selexipag and its active metabolite ACT-333679 is as follow:

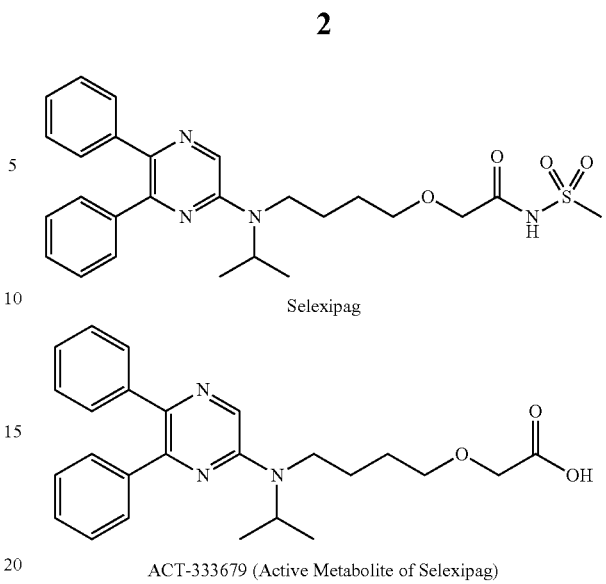

Selexipag

ACT-333679 (Active Metabolite of Selexipag)

Selexipag is currently sold under brand name UPTRAVI® and is available in a conventional immediate release dosage form. After an oral administration of conventional immediate release dosage form of Selexipag, i.e. UPTRAVI®, it absorbs rapidly and Cmax (Maximum plasma concentration) of Selexipag and its active metabolite are reached within about 1 hour and 2.75 hours, respectively, in fasting condition. However, many of the adverse events has been observed during the oral administration of conventional immediate release dosage form of the Selexipag and they are more worst in a fasting condition relative to a fed condition (Refer "medication guide of UPTRAVI®" as well as "Pharmacokinetics and Tolerability of the Novel Oral Prostacyclin IP Receptor Agonist Selexipag, Am. J. Cardiovasc Drugs. 2015; 15(3): 195-203").

Adverse events with onset after start of treatment are includes headache, nausea and vomiting. Due to the adverse event, i.e. issue of tolerability, therapy with the UPTRAVI® containing the Selexipag in immediate release form is recommended to start with 200 µg dose followed by increase the dose in increment of 200 µg twice daily, usually at weekly interval, to the highest tolerated dose up to 1600 µg twice daily. Overall, a non-tolerable most frequently reported adverse event is Headache with increasing frequency and intensity at single doses beyond 200 µg, particularly beyond 400 µg. As discussed in the "Pharmacokinetics and Tolerability of the Novel Oral Prostacyclin IP Receptor Agonist Selexipag" (Am. J. Cardiovasc Drugs. 2015; 15(3): 195-203"), 83% subject (5 out of 6 subjects), 33% subject (2 out of 6 subjects) and 17% subject (1 out of 6 subjects) reported Headache after administration of 800 µg, 600 µg and 200 µg Selexipag, respectively, in fasting condition. Hence, adverse events, which if severe, may lead to discontinuation of Therapy with the Selexipag. "Medical Review" section of UPTRAVI® submitted to USFDA disclosed that a total of 24% subjects (52 subjects out of 218 subjects) of the Selexipag treated patients had at least 1 adverse event leading to discontinuation of study drug in study AC-065A303.

As per the medication guide of UPTRAVI®, the most common adverse events reported more frequently after the oral administration of conventional immediate release dosage form of the Selexipag includes Headache in 65% subjects, Diarrhea in 42% subjects, Jaw pain in 26% subjects, Nausea in 33% subjects, Myalgia in 16% subjects, Vomiting in 18% subjects, Pain in Extremity in 17% subjects, Flushing in 12% subjects, Arthralgia in 11% subjects and Rash in 11% subjects out of 575 subjects. Interesting fact is that the adverse event is associated with high peak-trough fluctuation (plasma blood concentration) of Selexipag. This fact is supported by clinical study of UPTRAVI® in terms of differentiation in adverse events in Fed state compared to Fasting state. Compared to Fasting state, pharmacokinetic parameter Cmax is decreased 30% and Tmax extended 2.5 times in Fed state that leads to less adverse events observed when the Selexipag is taken after food (in Fed state). This explicitly indicate that slower rate of Selexipag absorption [Lower Cmax along with Extended Tmax (2.5 times longer)] leads to lower incident of adverse events, indicating that Controlled release dosage form of Selexipag is "Ideal Therapy" compared to conventional immediate release therapy. Therefore, present invention disclosed a controlled release formulation of Selexipag that exhibits significant advantages over the convention immediate release formulation of the Selexipag (UPTRAVI®) of the prior arts. The innovative controlled release formulation of the Selexipag improve a tolerability by reducing an incidence of side effects compared to the conventional immediate release formulation of the Selexipag (UPTRAVI®) as disclosed in the prior arts.

SUMMARY OF THE INVENTION

Preferred embodiment of this invention provides a controlled release pharmaceutical composition of a Selexipag or its active metabolite that improve tolerability by reducing incidence of side effect associated with the Selexipag or its active metabolite contained in the composition, wherein the composition after administration to a mammal in fasting condition providing a mean or median Tmax (time to reach maximum plasma concentration)
  a. of at least greater than 2 hours for the Selexipag, and/or
  b. of at least greater than 3.5 hours for the active metabolite of the Selexipag.

Preferred embodiment of this invention provide a controlled release pharmaceutical composition of a Selexipag or its active metabolite that improve tolerability by reducing incidence of side effect associated with the Selexipag or its active metabolite contained in the composition, wherein the composition comprising a release rate controlling ingredient in addition to the Selexipag or its active metabolite that control the releases of the Selexipag or its active metabolite at a rate such that a mean or median Tmax (time to reach maximum plasma concentration) attained after administration of the pharmaceutical composition to mammal in fasting condition is
  a. at least greater than about 2.5 hours for the Selexipag, and/or
  b. at least greater than about 4 hours for the active metabolite of the Selexipag.

It is an object of this invention to improve tolerability by reducing incidence of side effect associated with the Selexipag or its active metabolite. This is particularly important at high doses, for example at dose beyond 400 µg, at which the incidence of side effects can be relatively high. This object is effected by controlling the releases of the Selexipag or its active metabolite at a rate such that a mean or median Tmax (time to reach maximum plasma concentration) attained after administration of the pharmaceutical composition to mammal in fasting condition is at least greater than about 2.5 hours for the Selexipag, and/or at least greater than about 4 hours for the active metabolite of the Selexipag, thereby reducing the overall incidence as well as severity of the side effects and improving tolerability.

In a further embodiment, this invention provides a process for preparing controlled release pharmaceutical composition of the Selexipag or its active metabolite.

In a further embodiment, this invention provides a method for treating a Pulmonary Arterial Hypertension (PAH) with reduced incident of side effect, comprising administering the controlled release dosage form of the Selexipag or its active metabolite to a mammal, including a human patient, in need of such treatment which releases the Selexipag or its active metabolite according to the release rate described above.

DETAILED DESCRIPTION OF THE INVENTION

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

As used herein, the use of the word "a" or "an" when used in conjunction with the term "comprising" in the claims and/or the specification can mean "one," but it is also consistent with the meaning of "one or more," "at least one," and "one or more than one." Still further, the terms "having," "including," "containing", "comprising" and "comprises" are interchangeable, and one of skill in the art is cognizant that these terms are open-ended terms.

The term "about" or "approximately" means within an acceptable error range for the particular value as determined by one of ordinary skill in the art. For example, "about" can mean a range of up to 20%, up to 15%, up to 10%, up to 5%, or up to 1% of a given value.

The present invention disclosed a controlled release formulation of Selexipag or its active metabolite that exhibits significant advantages over the convention immediate release formulation of the Selexipag (UPTRAVI®) of the prior arts. The innovative controlled release formulation of the Selexipag improve a tolerability by reducing an incidence of side effects compared to the conventional immediate release formulation of the Selexipag (UPTRAVI®) as disclosed in the prior arts.

In the present invention, the term "Side effects" means those physiological effects to various systems in the body such as cardiovascular, nervous, digestive, and the body as a whole, which cause discomfort to the individual subject, and which are the direct result of the ingestion of the Selexipag or its active metabolite, for example Headache.

In the present invention, the term "reducing incidence of side effects" refers to a reduced incidence of side effects in a patient population, and not to a total absence of side effects, when measured in a comparable population consuming a conventional immediate release dosage form of Selexipag (UPTRAVI®) suitable for twice daily administration. As it is well known to those skilled in the art, even placebo dosage forms of UPTRAVI® (placebo dosage form of UPTRAVI® means dosage form comprising all ingredient present in UPTRAVI® in similar amount except the Selexipag) produce some measurable incidence of side effects. Thus, an improved side effect profile must be interpreted in light of the relevant art.

In the present invention, the term "drug" or "drug substance" refers to Selexipag or its active metabolite.

The term "administration" or "ingestion" as used herein is essentially synonymous with "swallowing".

The present invention is not limited to specific form of Selexipag or its active metabolite. Selexipag or its active metabolite can be employed in the pharmaceutical composition in any form including, but not limited to, in base form (as such), pharmaceutically acceptable form, any polymorphic form, anhydrous as well as hydrated form, solvates, co-crystal, crystalline or amorphous form, a single-component or multiple-component crystal, clathrate, etc. All such form of Selexipag or its active metabolite are within scope of this invention.

The pharmaceutical composition which constitute the subject matter of the invention are, as mentioned, controlled release formulations. The controlled release pharmaceutical composition of Selexipag or its active metabolite of the present invention can be administered to mammal by non-parenteral route, such as oral.

The term "controlled" is generic to "sustained", "pulsatile", "ascending" and "delayed". The pharmaceutical composition of Selexipag or its active metabolite possess at least one of the following characteristics are not "controlled release", and form no part of this invention:
1. provide mean or median Tmax less than 2 hours after administration to mammal in fasting condition, or
2. release more than 50% of their contained Selexipag or its active metabolite within 45 minutes or less when subjected to in-vitro dissolution testing at 37°±1° C. in 900 ml dissolution media having pH 6.8 in a USP Apparatus 2 (paddle) at 50 or 150 RPM.

For the purpose of this application, various embodiments of "controlled release dosage forms of Selexipag or its active metabolite" have been described as "sustained release" embodiments or "controlled release" embodiment, for ease of description. Without intending to be limiting, controlled release dosage forms of Selexipag or its active metabolite are those which slowly release Selexipag or its active metabolite; or release little or no Selexipag or its active metabolite for a predetermined time, then release Selexipag or its active metabolite quickly or in a sustained fashion; or release little or no Selexipag or its active metabolite in stomach but release Selexipag or its active metabolite quickly or in a sustained fashion in intestine. It will be appreciated by those skilled in the art that certain "sustained release" embodiments will also fall under the general rubric of "delayed release" or "pulsatile release" embodiments, and vice versa. For example, sustained release osmotic pump devices generally exhibit a "lag time" after ingestion, during which time the osmotic pressure in the device is increasing and during which time little or no drug is released. Thus, an osmotic pump device may be considered both a sustained release and a pulsatile release device.

In preferred embodiment, a controlled release pharmaceutical composition of a Selexipag or its active metabolite that improve tolerability by reducing incidence of side effect associated with the Selexipag or its active metabolite contained in the composition, wherein the composition comprising a release rate controlling ingredient in addition to the Selexipag or its active metabolite that control the releases of the Selexipag or its active metabolite at a rate such that a mean or median Tmax (time to reach maximum plasma concentration) attained after administration of the pharmaceutical composition to mammal in fasting condition is
  a. at least greater than about 2.5 hours for the Selexipag, and/or
  b. at least greater than about 4 hours for the active metabolite of the Selexipag,
wherein the release rate controlling ingredient is present in the composition as
  a) matrixing agent in which the Selexipag or its active metabolite is embedded, or
  b) coating layer surrounding the Selexipag or its active metabolite, or
  c) coating layer surrounding an inert core comprising the Selexipag or its active metabolite, wherein the inert core further comprising at least one pharmaceutically acceptable ingredient in addition to the Selexipag or its active metabolite, or
  d) a combination of at least two steps from step a), step b) and step c).

In preferred embodiment, a controlled release pharmaceutical composition of a Selexipag or its active metabolite that improve tolerability by reducing incidence of side effect associated with the Selexipag or its active metabolite contained in the pharmaceutical composition comprising one or more pharmaceutically acceptable carriers in addition to the Selexipag or its active metabolite,
  wherein a total amount of the pharmaceutically acceptable carriers contained in the pharmaceutical composition is not less than about 40% w/w of the total weight of the pharmaceutical composition,
  wherein at least one pharmaceutically acceptable carrier is a release rate controlling ingredient and a ratio of the Selexipag or its active metabolite to the release rate controlling ingredient is from about 1:0.1 to about 1:1000, and
  wherein the pharmaceutical composition releases the Selexipag or its active metabolite at a rate such that a mean or median Tmax (time to reach maximum plasma concentration) attained after administration of the pharmaceutical composition to mammal in fasting condition is
    a) at least greater than about 2.5 hours for the Selexipag, and/or
    b) at least greater than about 4 hours for the active metabolite of the Selexipag.

In preferred embodiment, a controlled release pharmaceutical dosage form of a Selexipag or its active metabolite that improve tolerability by reducing incidence of side effect associated with the Selexipag or its active metabolite contained in the dosage form comprising one or more pharmaceutically acceptable carriers in addition to the Selexipag or its active metabolite,
  wherein a total amount of the pharmaceutically acceptable carriers contained in the dosage form is not less than about 40% w/w of the total weight of the dosage form,
  wherein at least one pharmaceutically acceptable carrier is a release rate controlling ingredient and a ratio of the Selexipag or its active metabolite to the release rate controlling ingredient is from 1:0.1 to 1:1000, and
  wherein the dosage form having a release rate by weight of the Selexipag or its active metabolite in an aqueous medium is less than about 50% by weight of the Selexipag or its active metabolite release over the 45 minutes in the aqueous media, thereby a mean or median Tmax attained after administration of the dosage form to mammal in fasting condition is
    a) at least greater than about 2.5 hours for the Selexipag, and/or
    b) at least greater than about 4 hours for the active metabolite of the Selexipag, wherein the release rate is measured with USP apparatus 2 (paddle) at 50 RPM in 900 ml of an aqueous medium at a pH of 6.8±0.5 and temperature of 37°±1° C., wherein at least one side effect associated administration of the same amount of an immediate release dosage form of Selexipag or its active metabolite is reduced.

In preferred embodiment, a controlled release pharmaceutical composition of a Selexipag or its active metabolite that improve tolerability by reducing incidence of side effect associated with the Selexipag or its active metabolite contained in the composition, wherein the composition provide a release of Selexipag or it's active metabolite at an ascending release rate over an extended period of time such that a mean or median Tmax (time to reach maximum plasma concentration) attained after administration of the pharmaceutical composition to mammal in fasting condition is
- a. at least greater than about 2.5 hours for the Selexipag, and/or
- b. at least greater than about 4 hours for the active metabolite of the Selexipag.

In preferred embodiment, a controlled release pharmaceutical dosage form that improve tolerability by reducing incidence of side effect associated with a Selexipag or its active metabolite contained in the dosage form comprising a release rate controlling ingredient in addition to the Selexipag or its active metabolite that govern a release of the Selexipag or its active metabolite from the dosage form, wherein the dosage form after administration to a mammal in fasting condition providing
- a. a mean or median Tmax of at least greater than 2 hours for the Selexipag and/or at least greater than 3.5 hours for the active metabolite of the Selexipag, and/or
- b. at least 20% lower Cmax for Selexipag or it's active metabolite compared to Cmax obtained after administration of the same amount of an immediate release dosage form of Selexipag or its active metabolite in fasting condition, wherein the release rate controlling ingredient is present in the composition as
- a) matrixing agent in which the Selexipag or its active metabolite is embedded, or
- b) coating layer surrounding the Selexipag or its active metabolite, or
- c) coating layer surrounding an inert core comprising the Selexipag or its active metabolite, wherein the inert core further comprising at least one pharmaceutically acceptable ingredient in addition to the Selexipag or its active metabolite, or
- d) a combination of at least two steps from step a), step b) and step c).

A controlled release pharmaceutical dosage form that improve tolerability by reducing incidence of side effect associated with a Selexipag or its active metabolite contained in the dosage form comprising a release rate controlling ingredient in addition to the Selexipag or its active metabolite that govern a release rate of the Selexipag or its active metabolite from the dosage form, wherein the release rate controlling ingredient allow to release Selexipag or it's active metabolite from the dosage form in less than about 50% by weight of the Selexipag or its active metabolite contained in the dosage form over the 45 minutes in an aqueous medium, wherein the release rate is measured with USP apparatus 2 (paddle) at 50 or 150 RPM in 900 ml of an aqueous medium at a pH of 6.8±0.5 and temperature of 37°±1° C., wherein the release rate controlling ingredient is present in the composition as
- a. matrixing agent in which the Selexipag or its active metabolite is embedded, or
- b. coating layer surrounding the Selexipag or its active metabolite, or
- c. coating layer surrounding an inert core comprising the Selexipag or its active metabolite, wherein the inert core further comprising at least one pharmaceutically acceptable ingredient in addition to the Selexipag or its active metabolite, or
- d. a combination of at least two steps from step a), step b) and step c)

In preferred embodiment, for administration to the mammal by the non-parenteral route, the pharmaceutical composition can be in the form of a tablet, a capsule, a multiparticulates, suspension or a unit dose packet (sometimes refer to in the art as a "sachet"). The term "multiparticulate" is intended to embrace a pharmaceutical composition or dosage form comprising a multiplicity of particles whose totality represents the intended therapeutically useful dose of Selexipag or its active metabolite. The particles generally are of a diameter from about 50 microns to about 0.3 cm, with a preferred range of 100 µM to 1.5 mm.

In preferred embodiment, the amount of Selexipag or its active metabolite contained within the dosage form is preferably at least 0.2 mg or more and most preferably at least 0.4 mg or more. The term "dosage form" or "dosage unit" is used to refer to drug delivery system of the pharmaceutical composition comprising a predetermined quantity (therapeutically effective dose) of drug substance and suitable as unitary dosages for administration to human patients to attain the desired therapeutic effect.

The controlled release pharmaceutical composition of this invention can be widely implemented. For purposes of discussion, not limitation, the many embodiments hereunder can be grouped into classes according to design and principle of operation.

In preferred embodiment, a first class include matrix system, in which Selexipag or its active metabolite is embedded or suspended or dispersed within a matrix of controlled release ingredient which serve to retard the release of Selexipag or its active metabolite into an aqueous environment (i.e., the lumenal fluid of the GI tract, or dissolution media). When Selexipag or its active metabolite is dispersed in a matrix of this sort, release of the Selexipag or its active metabolite takes place principally from the surface of the matrix. Thus, the Selexipag or its active metabolite is released from the surface of the matrix after it diffuses through the matrix or when the surface of the matrix erodes, exposing the drug. In some embodiments, both mechanisms can operate simultaneously. The matrix systems may be large, i.e., tablet sized (about 1 cm), or small (<0.3 cm). The system may be unitary (e.g, a bolus), or may comprise a plurality of particles, referred to herein as a multiparticulate. A multiparticulate can be compressed with other pharmaceutically acceptable ingredient to form a tablet, or can be packed in capsule or sachet, or can be used to fabricate suspension (such as powder for suspension) or liquid formulation. A multiparticulate can have numerous formulation applications such as can be administered after mixing with food or juice.

The size of the matrix system can affect the rate of Selexipag or its active metabolite release, therefore, a large matrix system such as a tablet will, in general, have a different composition, i.e. comprising different controlled release ingredient or different amount of same controlled release ingredient, from a small one such as a multiparticulate. For purposes of further illustration, to obtain a sustained-release matrix in a particle of about 50 µm in diameter, a matrix material of a polymer such as cellulose acetate, ethyl cellulose, wax or a similar material will likely be required. By contrast, in order to obtain sustained-release in a large (e.g., 1 cm) device, a material which is mostly liquid-like (e.g., a hydrogel, see below) will likely be required. For devices of an intermediate size, e.g., about 5 mm in diameter, a matrix material of intermediate characteristics can be employed. It is also noted that the effective diffusion coefficient of Selexipag or its active metabolite may be increased to the desired value by the addition of plasticizers, pores, or pore-inducing additives, as known in the art. Slowly-hydrating materials may also be used to give the desired intermediate diffusion rates. The multiplicity of variables affecting release of Selexipag or its active metabolite from matrix devices permits abundant flexibility in the design of devices of different materials, sizes, and release times. Certain examples of modifications of Selexipag or its active metabolite release profiles from the specific embodiments of the examples within the scope of this invention are disclosed below.

In one embodiment, a matrix multiparticulate, comprises a plurality of Selexipag or its active metabolite containing particles, each particle comprising a mixture of Selexipag or its active metabolite with one or more controlled release ingredient selected to form a matrix capable of limiting the dissolution rate of the Selexipag or its active metabolite into an aqueous medium. The matrix materials useful for this embodiment are generally water-insoluble materials or slowly water soluble material. If needed, the matrix materials may optionally be formulated with water-soluble materials which can be used as binders or as permeability-modifying agents.

A preferred process for manufacturing matrix multiparticulates is the extrusion/spheronization process. For this process, the Selexipag or its active metabolite is wet-massed with a binder, extruded through a perforated plate or die, and placed on a rotating disk. The extrudate ideally breaks into pieces which are rounded into spheres, spheroids, or rounded rods on the rotating plate.

A further preferred process for manufacturing matrix multiparticulates is the preparation of melt granules. In this process, a desired amount of Selexipag or its active metabolite is stirred with matrix material having low melting point at elevated temperature or above melting temperature of the matrix material to form a homogeneous mixture, cooled and then forced through a screen to form granules. Melt granules can be prepared by applying heat while mixing Selexipag or its active metabolite with matrix material having low melting point in granulator such as rapid mixture granulator.

A further preferred process for manufacturing matrix multiparticulates involves using an organic solvent to aid mixing of the Selexipag or its active metabolite with the matrix material. This technique can be used when it is desired to utilize a matrix material with an unsuitably high melting point that, if the material were employed in a molten state, would cause decomposition of the drug or of the matrix material, or would result in an unacceptable melt viscosity, thereby preventing mixing of Selexipag or its active metabolite with the matrix material. Selexipag or its active metabolite and matrix material may be combined with a modest amount of solvent to form a paste, and then forced through a screen to form granules from which the solvent is then removed. Alternatively, Selexipag or its active metabolite and matrix material may be combined with enough solvent to completely dissolve the matrix material and the resulting solution spray dried to form the particulate dosage form. This technique is preferred when the matrix material is a high molecular weight synthetic polymer such as a cellulose ether or cellulose ester or wax.

Once formed, Selexipag or its active metabolite matrix multiparticulates may be blended with compressible excipients and the blend compressed to form a tablet. Disintegrants are also usefully employed. Tablets prepared by this method disintegrate when placed in an aqueous medium, thereby exposing the multiparticulate matrix which releases Selexipag or its active metabolite. Selexipag or its active metabolite matrix multiparticulates may be filled in capsule or sachet or can be mixed with pharmaceutically acceptable additive to form a powder for suspension. Selexipag or its active metabolite matrix multiparticulates can be administered after sprinkling on food or juice.

A further embodiment of a matrix system has the form of a matrix tablet containing Selexipag or its active metabolite and an amount of matrixing material sufficient to provide a useful degree of control over the Selexipag or its active metabolite dissolution. The matrix tablet includes hydrophilic matrix, hydrophobic matrix, or any combination thereof. Hydrophilic polymer (Water soluble), hydrophobic material (water insoluble) or combination thereof are useful for forming the matrix. The Selexipag or its active metabolite is released by diffusion from the matrix, by erosion of the matrix or combination thereof. The Selexipag or its active metabolite dissolution rate from these matrix tablets may be controlled by the amount and/or the solubilisation rate of matrixing material employed. The dissolution rate may also be controlled by the use of water-soluble additives such as sugars, salts, or soluble polymers. In general, increasing the fraction of soluble material in the formulation increases the release rate.

The matrix systems as a class often exhibit non-constant release of the drug from the matrix. This result may be a consequence of the diffusive mechanism of drug release, and modifications to the geometry of the dosage form can be used to advantage to make the release rate of the drug more constant. In one embodiment, a Selexipag or its active metabolite matrix tablet is coated with an water insoluble coating in full or in part (on one or both tablet faces, or on the tablet radial surface). The water permeable coating optionally comprising pore former or flux enhancer such as water soluble additives like sugars, salts, or soluble polymers. The water insoluble coating may optionally comprising one or more passageways for drug transport from the composition to aqueous environment. A passageway for drug transport is produced by drilling a hole in coating, or removing one or more strip through the coating film, or cutting one or more slits through the coating film. In preferred embodiment, the water insoluble coating comprising at least one water insoluble material.

A further sustained release matrix system comprises Selexipag or its active metabolite dispersed in a hydrogel matrix. This embodiment differs from the hydrophilic matrix tablet discussed above in that the hydrogel of this embodiment is not a compressed tablet of erodible granular material, but rather a monolithic polymer network. As known in the art, a hydrogel is a water-swellable network polymer. Preferred materials for forming hydrogels include hydrophilic vinyl and acrylic polymers, polysaccharides such as calcium alginate, and poly(ethylene oxide). Especially preferred are poly(2-hydroxyethyl methacrylate), poly(acrylic acid), poly(methacrylic acid), poly(N-vinyl-2-pyrrolidinone), poly(vinyl alcohol) and their copolymers with each other and with hydrophobic monomers such as methyl methacrylate, vinyl acetate, and the like. Also preferred are hydrophilic polyurethanes containing large poly(ethylene oxide) blocks. Other preferred materials include hydrogels comprising interpenetrating networks of polymers, which may be formed by addition or by condensation polymerization, the components of which may comprise hydrophilic and hydrophobic monomers such as those just enumerated.

In preferred embodiment, a second class of Selexipag or its active metabolite controlled release pharmaceutical composition of this invention includes membrane-moderated or reservoir systems. In this class, a reservoir (inert core) of Selexipag or its active metabolite is surrounded by a rate-limiting membrane (controlled release coating). These individual reservoir system dosage forms may be large, as in the case of a tablet or capsule containing a single large reservoir (inert core), or multiparticulate, as in the case of a plurality of reservoir (inert core) particles, each individually coated with the membrane. The coating can be non-porous, yet permeable to Selexipag or its active metabolite (for example Selexipag or its active metabolite may diffuse directly through the membrane), or it may be porous. As with other embodiments of this invention, the particular mechanism of transport is not believed to be critical.

Controlled release coatings as known in the art may be employed to fabricate the membrane, especially polymer coatings, such as a cellulose ester or ether, an acrylic polymer, vinyl acetate (such as polyvinyl acetate) or its copolymer or a mixture of polymers, on a reservoir of Selexipag or its active metabolite. The polymer may be applied as a solution in an organic solvent or an aqueous solvent or as an aqueous dispersion or latex. The coating operation may be conducted in standard equipment such as a fluid bed coater, a Wurster coater, or a rotary bed coater or conventional coater.

If desired, the permeability of the coating may be adjusted by blending of two or more materials. A particularly useful process for tailoring the porosity of the coating comprises adding a pre-determined amount of a finely-divided water-soluble material, such as sugars or salts or water-soluble polymers to a solution or dispersion (e.g., an aqueous latex) of the membrane-forming polymer to be used. When the dosage form is ingested into the aqueous medium of the GI tract, these water soluble membrane additives are leached out of the membrane, leaving pores which facilitate release of the drug. The membrane coating can also be modified by the addition of plasticizers, as known in the art.

A particularly useful variation of the process for applying a membrane coating comprises dissolving the coating polymer in a solvent or mixture of solvents chosen such that as the coating dries, a phase inversion takes place in the applied coating solution, resulting in a membrane with a porous structure. Numerous examples of this type of coating system are given in European Patent Specification 0357369 B1, published Mar. 7, 1990, herein incorporated by reference. In general, a support for mechanically strengthening the membrane is not required.

The morphology of the membrane is not of critical importance so long as the permeability characteristics enumerated herein are met. The membrane can be amorphous or crystalline. It can have any category of morphology produced by any particular process and can be, for example, an interfacially-polymerized membrane (which comprises a thin rate-limiting skin on a porous support), drug permeable membrane, asymmetric membrane, a porous hydrophilic membrane, a porous hydrophobic membrane, a hydrogel membrane, an ionic membrane, and other such materials which are characterized by controlled permeability to Selexipag or its active metabolite.

A single larger reservoir such as tablet or capsule can be manufactured by the process known in this art using, in addition of the drug substance, one or more pharmaceutical acceptable material which include, but not limited to, filler, binder, osmotic agents, hydrophilic, swellable or hydrogel polymer, lubricant, glidant, surfactant, and like.

A preferred embodiment of the class of reservoir systems comprises a multiparticulate, wherein each particle is coated with a polymer designed to yield controlled release of Selexipag or its active metabolite. The multiparticulate particles each comprise Selexipag or its active metabolite and one or more excipients as needed for fabrication and performance including ion-exchange resin to form drug-ion-exchange resin complex. The size of individual particles is generally between about 50 μm and about 3 mm, although beads of a size outside this range may also be useful.

Reservoir system Selexipag or its active metabolite multiparticulates may be prepared using techniques known to those skilled in the art, including, but not limited to, the techniques of extrusion and spheronization, wet granulation, fluid bed granulation, rotary bed granulation and forming complexation of drug with ion-exchange resin (drug-ion exchange resin complex). In addition, the beads may also be prepared by building the Selexipag or its active metabolite composition (drug plus excipients) up on a seed core (such as a non-pareil seed) by a drug-layering technique such as powder coating or by applying the Selexipag or its active metabolite composition by spraying a solution or dispersion of Selexipag or its active metabolite in an appropriate binder solution onto seed cores (such as sugar sphere, microcrystalline cellulose sphere, etc) in a fluidized bed such as a Wurster coater or a rotary processor. Another method for manufacturing the multiparticulate cores of this embodiment is the extrusion and spheronization process, as previously discussed for matrix multiparticulates.

A controlled release coating as known in the art, especially polymer coatings, may be employed to fabricate the membrane, as previously discussed, for reservoir systems. Suitable and preferred polymer coating materials, equipment, and coating methods also include those previously discussed.

The rate of Selexipag or its active metabolite release from the coated multiparticulates can also be controlled by factors such as the composition and binder content of the drug-containing core (reservoir), the thickness and permeability of the coating, and the surface-to-volume ratio of the multiparticulates. It will be appreciated by those skilled in the art that increasing the thickness of the coating will decrease the release rate, whereas increasing the permeability of the coating or the surface-to-volume ratio of the multiparticulates will increase the release rate. If desired, the permeability of the coating may be adjusted by blending of two or more materials. A useful series of coatings comprises mixtures of water-insoluble and water-soluble polymers, for example, ethylcellulose and hydroxypropyl methylcellulose, respectively. A particularly useful modification to the coating is the addition of finely-divided water-soluble material, such as sugars or salts. When placed in an aqueous medium, these water soluble membrane additives are leached out of the membrane, leaving pores which facilitate delivery of the drug. The membrane coating may also be modified by the addition of plasticizers, as is known to those skilled in the art. A particularly useful variation of the membrane coating utilizes a mixture of solvents chosen such that as the coating dries, a phase inversion takes place in the applied coating solution, resulting in a membrane with a porous structure.

In preferred embodiment, a third class of Selexipag or its active metabolite controlled release pharmaceutical composition includes the osmotic delivery devices or "osmotic pumps" as they are known in the art. Osmotic pumps comprise a core containing an osmotically effective composition surrounded by a semipermeable membrane. The term "semipermeable" in this context means that water can pass through the membrane, but solutes dissolved in water cannot. In use, when placed in an aqueous environment, the device imbibes water due to the osmotic activity of the core composition. Owing to the semipermeable nature of the surrounding membrane, the contents of the device (including the drug and any excipients) cannot pass through the non-porous regions of the membrane and are driven by osmotic pressure to leave the device through an opening or passageway pre-manufactured into the dosage form or, alternatively, formed in situ in the GI tract as by the bursting of intentionally-incorporated weak points in the coating under the influence of osmotic pressure. The osmotically effective composition includes water-soluble species, which generate a colloidal osmotic pressure, and water-swellable polymers.

Materials useful for forming the semipermeable membrane include polyamides, polyesters, and cellulose derivatives. Preferred are cellulose ethers and esters. Especially preferred are cellulose acetate, cellulose acetate butyrate, and ethyl cellulose. Especially useful materials include those which spontaneously form one or more exit passageways, either during manufacturing or when placed in an environment of use. These preferred materials comprise porous polymers, the pores of which are formed by phase inversion during manufacturing, as described above, or by dissolution of a water-soluble component present in the membrane.

A preferred embodiment of this class of osmotic delivery devices consists of a coated mono-layer, bi-layer or tri-layer tablet. The coated monolayer tablet comprising a single layer tablet core containing the Selexipag or its active metabolite composition and a semipermeable coating surrounding the core tablet contains one or more exit passageways. The coated bilayer tablet comprising (1) a tablet core consists of two layers: one layer containing the Selexipag or its active metabolite composition and another layer consisting of an expandable hydrogel (fluid expandable polymer), with or without additional osmotic agents; and (2) a semipermeable coating surrounding the core tablet contains one or more exit passageways in communication with the Selexipag or its active metabolite containing layer for delivering the drug composition. The coated trilayer tablet comprising (1) a tablet core consists of three layers: first layer comprising the Selexipag or its active metabolite composition, second layer comprising the Selexipag or its active metabolite composition and another layer consisting of an expandable hydrogel (fluid expandable polymer), with or without additional osmotic agents, wherein % weight of the Selexipag or its active metabolite in the second layer with respect to total weight of the second layer is higher than % weight of the Selexipag or its active metabolite in the first layer with respect to total weight of the first layer, and (2) a semipermeable coating surrounding the core tablet contains one or more exit passageways in communication with the first Selexipag or its active metabolite containing layer for delivering the drug composition, wherein the trilayer coated tablet deliver the Selexipag or its active metabolite at ascending rate over the extended period of time, for at least about 4 hours or more. The layer of Selexipag or its active metabolite composition comprises, in addition to the drug substance, one or more pharmaceutical acceptable material which include, but not limited to, filler, binder, osmotic agents, osmo-polymer (fluid expandable polymer such as polyethylene oxide, hydroxyethyl cellulose and like), hydrophilic or swellable polymer, lubricant, glidant, surfactant, and like.

The rate of Selexipag or its active metabolite delivery is controlled by such factors as the permeability and thickness of the coating, the water activity of the hydrogel layer, and the surface area of the device. Those skilled in the art will appreciate that increasing the thickness of the coating will reduce the release rate, whereas increasing the permeability of the coating or the water activity of the hydrogel layer or the surface area of the device will increase the release rate.

The exit passageway must be located on the side of the tablet containing the Selexipag or its active metabolite composition. There may be more than one such exit passageway. The exit passageway may be produced by mechanical or by laser drilling, or by creating a difficult-to-coat region on the tablet by use of special tooling during tablet compression.

The osmotic pump also includes osmotic capsule. The method of manufacturing osmotic capsule as well as osmotic tablets is well known in the art, are described in detailed in many patents issued to Alza Corp as well as in "Osmotic drug delivery: a review of the patent literature", Journal of Controlled Release 35 (1995) 1-21.

In preferred embodiment, a forth class Selexipag or its active metabolite controlled release pharmaceutical composition comprising pH sensitive coat surrounding any one of the first class, the second class and third class controlled release pharmaceutical composition of Selexipag or its active metabolite discussed aforesaid, preferably the coat of a pH sensitive polymer which is substantially insoluble and impermeable at the pH of the stomach, and which is more soluble and permeable at the pH of the small intestine. Preferably, the coating polymer is substantially insoluble and impermeable at pH<5.0, and water soluble at pH>5.0. The pH-sensitive polymers which are relatively insoluble and impermeable at the pH of the stomach, but which are more soluble and permeable at the pH of the small intestine and colon include polyacrylamides, phthalate derivatives such as acid phthalates of carbohydrates, amylose acetate phthalate, cellulose acetate phthalate, other cellulose ester phthalates, cellulose ether phthalates, hydroxypropylcellulose phthalate, hydroxypropylethylcellulose phthalate, hydroxypropylmethylcellulose phthalate, methylcellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinylacetate phthalate copolymer, styrene and maleic acid copolymers, polyacrylic acid derivatives such as acrylic acid and acrylic ester copolymers, polymethacrylic acid and esters thereof, poly acrylic methacrylic acid copolymers, shellac, and vinyl acetate and crotonic acid copolymers. The pH sensitive coat comprising an amount of polymer from about 5 to about 50% of total weight of the pharmaceutical composition.

In preferred embodiment, a fifth class Selexipag or its active metabolite controlled release pharmaceutical composition comprising pH sensitive coat surrounding a reservoir of Selexipag or its active metabolite. In this class, a reservoir of Selexipag or its active metabolite is surrounded by the pH sensitive coat. These individual reservoir system dosage forms may be large, as in the case of a tablet or capsule containing a single large reservoir, or multiparticulate, as in the case of a plurality of reservoir particles, each individually coated with the pH sensitive polymer.

Method of manufacturing the reservoir of Selexipag or its active metabolite are described aforesaid in the second class of Selexipag or its active metabolite controlled release pharmaceutical composition.

In preferred embodiment, the first class, the second class, the third class, the forth class and the fifth class controlled release pharmaceutical composition of Selexipag or its active metabolite described above further comprising immediate release dose of Selexipag or its active metabolite to provide an initial rapid onset of the drug action. The immediate release dose of Selexipag or its active metabolite can be provided in the pharmaceutical composition in form of coating layer or in form of separate layer in multilayer tablet or in form of granules.

In the present invention, the terms "material", "excipient", "ingredient" and "component" are interchangeable, and one of skill in the art is cognizant that these terms are open-ended terms.

According to present invention, a controlled release materials includes water-insoluble materials, hydrophilic polymer, swellable polymer, hydrogel polymer, water soluble polymer and pH sensitive polymer. In the present invention, the term "controlled release material" or "release rate controlling ingredient" or "release retardant" are interchangeable. The term "controlled release material" refers to any material that control or sustained the release rate of Selexipag or it's active metabolite from a dosage form. In preferred embodiment, the dosage form or pharmaceutical composition comprising controlled release material in about 0.01% w/w to about 99.9% w/w, preferably about 1% w/w to about 95% w/w, more preferably about 2% w/w to about 93% w/w, most preferably about 10% w/w to about 85% w/w or particularly preferably about 15% w/w to about 75% w/w of total weight of the dosage form or total weight of the pharmaceutical composition.

In the present invention, the term "water insoluble material" or "hydrophobic material" refers to a component which is insoluble in water. A water insoluble material includes wax and water insoluble polymer. Suitable water insoluble ingredient includes natural, synthetic or semi synthetic ingredient. Natural, synthetic or semi synthetic water insoluble ingredient include, but are not to be limited, cellulose derivatives include cellulose acetate, cellulose acetate butyrate, cellulose triacetate, microcrystalline cellulose, ethyl cellulose; wax include microcrystalline wax, beeswax, glycowax, castor wax, carnauba wax, glycerol monostearate, glycerol palmitostearate; oil include hydrogenated vegetable oil, hydrogenated castor oil, vegetable oil, stearyl alcohol, acetylated hydrogenated soybean oil glycerides, castor oil; glycerol behenic acid ester, glyceryl monooleate, glyceryl monostearate, propylene glycol monostearate, cetyl alcohol, natural and synthetic glycerides, fatty acids, fatty alcohol, lipid, methacrylic acid derivatives such as polymethacrylate and its copolymer (such as polymer under brand name Eudragit®), polyvinyl acetate, copolymers of vinyl pyrrolidone and vinyl acetate; vinyl acetate and copolymer thereof, ethyl vinyl acetate, modified starch like pregelatinised starch, polylactic acid or polyglycolic acid and copolymers thereof, methacrylates, cocoa butter, macrogol Stearate, diethylene glycol monostearate, polyoxyethylene 50 stearate, and mixtures thereof. In preferred embodiment, the dosage form or pharmaceutical composition comprising water insoluble material or hydrophobic material in about 0.01% w/w to about 99.9% w/w, preferably about 1% w/w to about 95% w/w, more preferably about 2% w/w to about 93% w/w, most preferably about 10% w/w to about 85% w/w or particularly preferably about 15% w/w to about 75% w/w of total weight of the dosage form or total weight of the pharmaceutical composition.

A suitable hydrophilic polymer, swellable polymer, hydrogel polymer and water soluble polymer consisting of natural, semi-synthetic or synthetic ingredient which includes, but not limited to, gum such as xanthan gum, acacia gum, diutan gum, tragacanth, gellan gum, guar gum, fenugreek gum, locust bean gum, pullulan, welan gum; polysaccharide; polymer includes, but not limited to, cellulose derivatives such as carboxymethyl cellulose, cellulose ether (such as hydroxyethyl cellulose, hydroxypropylmethyl cellulose, hydroxypropyl cellulose, etc), polyalkylene oxide and its co-polymer such as polyethylene oxide, copolymer of ethylene oxide-propylene oxide, polycarboxylic acid such as polyacrylic acid, polyolefinic alcohol (such as polyvinyl alcohol), or a polyvinyl lactam such as, e.g., polyvinylpyrrolidone, polyvinyl caprolactam, alginic acid and its derivative, methacrylic acid and its copolymer (such as polymer under brand name Eudragit®), polyacrylic acid and copolymer thereof (such as carbomer); protein or polypeptide such as gelatin, albumin, polylysine, soy protein; starch or its derivative; and like. Polysaccharides are polymeric carbohydrate molecules composed of long chains of monosaccharide units bound together by glycosidic linkages and on hydrolysis give the constituent monosaccharides or oligosaccharides. They range in structure from linear to highly branched. Examples include storage polysaccharides such as starch and glycogen, and structural polysaccharides such as cellulose and chitin. In certain embodiment, polymer, gum, polysaccharide and starch can be used as binder, pore former, flux enhancer and osmo-polymer (osmotic agent) like. In preferred embodiment, the dosage form or pharmaceutical composition comprising swellable polymer, hydrogel polymer or water soluble polymer in about 0.01% w/w to about 99.9% w/w, preferably about 1% w/w to about 95% w/w, more preferably about 2% w/w to about 93% w/w, most preferably about 10% w/w to about 85% w/w or particularly preferably about 15% w/w to about 75% w/w of total weight of the dosage form or total weight of the pharmaceutical composition.

In the present invention, the term "hydrophilic material" refers to a component which is soluble in water. The hydrophilic material includes, but not limited to, hydrophilic polymer, swellable polymer and hydrogel polymer, salt, sugar, acid, base and like.

The controlled release pharmaceutical composition further comprising one or more pharmaceutically acceptable additive depending on its functionality in the pharmaceutical composition which includes, but not limited to, filler, diluent, disintegrant, anti-tacking agent, binder, glidant, surfactant, wetting agent, lubricant, anti-oxidant, plasticizer, sweetener, coloring agent, sugar, salt, acid and osmotic agent.

Fillers or diluents such as cellulose derivatives, mono, di or tri basic calcium phosphate, sugar, carbohydrate, starch derivatives, acid or base, and like. Filler or diluent refers to material that is used to increase the bulk volume of a dosage form and/or to improve content uniformity of a dosage form. Filler or diluent does not inter Disintegrant may be highly/rapidly swellable, moderately swellable or slowly swellable such as vinylpyrrolidone polymers such as crospovidon, cellulose and cellulose derivatives, sodium starch glycolate, starch and starch derivatives, resins, and like Suitable anti-tacking agent is selected from the group consisting of, but are not limited to, stearates, stearic acid, vegetable oil, waxes, a blend of magnesium stearate and sodium lauryl sulfate, boric acid, surfactants, sodium benzoate, sodium acetate, sodium chloride, DL-Leucine, polyethylene glycol, sodium oleate, sodium lauryl sulfate, magnesium lauryl sulfate, talc, corn starch, amorphous silicon dioxide, syloid, metallic stearates, Vitamin E, Vitamin E TPGS, silica and combinations thereof.

Suitable binder include, but are not to be limited, cellulose derivatives include, but are not limited to be, methyl cellulose, hydroxypropyl methylcellulose, hydroxyethyl cellulose, hydroxypropyl cellulose, hydroxyethyl methylcellulose, ethylhydroxyethylcellulose, ethylmethylcellulose, hydroxymethylcellulose, hydroxymethylpropylcellulose, sodium carboxymethylcellulose, polyacrylamide derivatives, methacrylic acid derivatives, vinyl pyrrolidone polymers such as polyvinylpyrrolidone, starch derivative, polyalkylene oxide and copolymer thereof, alkylene oxide homopolymers, gums of plant, animal, mineral or synthetic origin, polyacrylic acid and copolymer thereof, polyvinyl alcohols, polyethylene glycol, poloxamer, and mixtures thereof.

Suitable glidants and lubricants may be incorporated such as stearic acid, metallic stearates, talc, waxes, and glycerides with high melting temperatures, colloidal silica, sodium stearyl fumarate, polyethyleneglycols, and alkyl sulphates.

Suitable plasticizers includes, but are not limited to, triacetin, triethyl acetate, acetylated monoglyceride, olive oil, acetyl tributyl citrate, acetyl triethyl citrate, glycerin, sorbitol, polyethylene glycol, polypropyleneglycol and like.

Stabilizer, such as anti-oxidant, to inhibit or retard oxidative drug decomposition during storage of the pharmaceutical composition.

Natural or synthetic sweeteners include, but note limited to, mannitol, sorbitol, saccharose, saccharine, aspartame, acelsulphame K, or cyclamate.

Preferred coloring agent includes D&C dye/lake, FD&C dye, an FD&C lake, caramel, ferric oxide, a natural coloring agent, and a combination thereof. The amount of coloring agent used will vary as desired. Preferably the composition is non-toxic, edible, stable in light and air and free of potential hazards to human health.

Preferred sugars include dextrose, glucose, arabinose, ribose, arabinose, xylose, lyxose, xylol, allose, altrose, inositol, glucose, sorbitol, mannose, gulose, glycerol, idose, galactose, talose, trehalose, mannitol, erythritol, ribitol, xylitol, maltitol, isomalt, lactitol, sucrose, raffinose, maltose, fructose, lactose, dextrin, dextran, amylase and xylan.

Water soluble salts include sodium chloride, potassium chloride, calcium chloride or magnesium chloride, lithium chloride, lithium, sodium or potassium hydrogen phosphate, lithium, sodium or potassium dihydrogen phosphate, salts of organic acids such as sodium or potassium acetate, sodium bicarbonate, magnesium succinate, sodium benzoate, sodium citrate or sodium ascorbate.

Preferred acids include ascorbic acid, 2-benzene carboxylic acid, benzoic acid, fumaric acid, citric acid, maleic acid, serbacic acid, sorbic acid, edipic acid, edetic acid, glutamic acid, toluene sulfonic acid, water-soluble amino acids such as glycine, leucine, alanine, or methionine and tartaric acid; and like.

Osmotic agent includes sugar and salts as described above.

Surfactants and Wetting agents include, but are not limited to heptadecaethylene oxycetanol, lecithins, sorbitol monooleate, polyoxyethylene sorbitol monooleate, polyoxyethylene stearate, polyoxyethylen sorbitan monolaurate, benzalkonium chloride, nonoxynol 10, oxtoxynol 9, polysorbates for example 20, 40, 60 or 80, sorbitan monopalmitate, sodium salts of fatty alcohol-sulfates such as sodium lauryl sulfate, sodium dodecylsulfate, sodium salts of sulfosuccinates such as sodium dioctylsulfosuccinate, partially esters of fatty acids with alcohols such as glycerine monostearate, partially esters of fatty acids with sorbitans such as sorbitan monolaurate, partially esters of fatty acids with polyhydroxyethylene sorbitans such as polyethyleneglycol sorbitan monolaurate, -monostearate or -monooleate, ethers of fatty alcohols with polyhydroxyethylene, esters of fatty acids with polyhydroxyethylene, copolymers of ethylenoxide and propylenoxide (Pluronic®) and ethoxylated triglycerides.

Functionality of pharmaceutically acceptable additive and tentative range for concentration to be used in the pharmaceutical dosage form according to the functionality also described in Handbook of Pharmaceutical Excipients, $6^{th}$ Edition, Edited by Raymond C Rowe, Paul J Sheskey and Marian E Quinn.

The above listed ingredients are for information only, which does not limit the scope of the present invention. Any ingredient which is used in the pharmaceutical composition that fulfil the subject matter of the present invention are within the scope of the present invention.

The present invention is not limited to art of fabricating controlled release dosage form of Selexipag or its active metabolite, in other word, an ordinary skill in this art can also manufactured controlled release dosage form of Selexipag or its active metabolite by any other method than described above.

EXAMPLES

The invention will now be illustrated by the following examples which are not to be taken as limiting. In general, the examples demonstrate the preparation of controlled-release pharmaceutical composition of Selexipag or its active metabolite within the scope of this invention.

Example 1

Matrix Formulation (Tablet Form):

| Sr. No. | Ingredient Name | % w/w |
| --- | --- | --- |
| 1 | Selexipag | 0.67 |
| 2 | Mannitol | 66.66 |
| 3 | Hydroxypropylmethyl Cellulose (HPMC) | 30.17 |
| 4 | Colloidal Silicon Dioxide | 1.50 |
| 5 | Magnesium Stearate | 1.00 |

Manufacturing Procedure:
1. Co-sift Selexipag with mannitol through appropriate screen.
2. Sift Hydroxypropylmethyl cellulose, colloidal silicon dioxide and magnesium stearate separately through appropriate screen.
3. Blend the step (1) Selexipag and mannitol with the step (2) HPMC and colloidal silicon dioxide for suitable time period.
4. Blend the step (2) magnesium stearate with the step (3) material for suitable period of time.
5. Compress the tablets using the step (4) material on compression machine using appropriate tooling (punches).

Example 2

Coated Reservoir Formulation (Multiparticulate Form)

| Sr. No. | Ingredient Name | % w/w |
|---|---|---|
| | Reservoir Components (Sustained Release) | |
| 1 | Selexipag | 0.67 |
| 2 | Mannitol | 41.28 |
| 3 | Hydroxypropylmethyl Cellulose (HPMC) | 40.00 |
| 4 | Colloidal Silicon Dioxide | 0.83 |
| 5 | Magnesium Stearate | 0.56 |
| | Coating Components (Sustained Release) | |
| 6 | Ethyl Cellulose | 6.67 |
| 7 | Hydroxypropylmethyl Cellulose (HPMC) | 4.44 |
| | Immediate Release Drug Coat | |
| 8 | Selexipag | 0.44 |
| 9 | Hydroxypropylmethyl Cellulose (HPMC) | 3.72 |
| 10 | Polyethylene Glycol (PEG) | 1.39 |

Manufacturing Procedure:
A. Preparation of Reservoir Core
  1. Co-sift Selexipag with mannitol through appropriate screen.
  2. Sift Hydroxypropylmethyl cellulose, colloidal silicon dioxide and magnesium stearate separately through appropriate screen.
  3. Blend the step (1) Selexipag and mannitol with the step (2) HPMC and colloidal silicon dioxide for suitable time period.
  4. Blend the step (2) magnesium stearate with the step (3) material for suitable period of time.
  5. Compress the mini-tablets using the step (4) material on compression machine using 2 mm tooling (punches).
B. Sustained Release Coat
  6. Preparation of Coating Solution: Add one by one coating components, ethyl cellulose following 3PMC, in mixture of dichloromethane and isopropyl alcohol (1:1) and stir it till get clear solution.
  7. Coat the step (5) minitablets in coating machine using the step (6) coating solution.
C. Immediate Release Drug Over Coat
  8. Preparation of Coating Solution: Add one by one coating components, Selexipag followed by PEG followed by HPMC, in water and stir it for at least 60 minutes.
  9. Coat the step (7) minitablets in coating machine using the step (8) coating solution.

Example 3

Osmotic Formulation (for Ascending Drug Release Profile)

| Sr. No. | Ingredient Name | % w/w |
|---|---|---|
| | Trilayer Tablet Core (First Layer) | |
| 1 | Selexipag | 0.59 |
| 2 | Polyethylene Oxide (Polyox WSR N80) (PEO) | 25.95 |
| 3 | Povidone (PVP) | 2.44 |
| 4 | Ferric Oxide Red (color) | 0.05 |
| 5 | Magnesium Stearate | 0.24 |
| | Trilayer Tablet Core (Second Layer) | |
| 6 | Selexipag | 0.78 |
| 7 | Polyethylene Oxide (Polyox WSR N80) (PEO) | 16.98 |
| 8 | Povidone (PVP) | 1.59 |
| 9 | Brilliant Blue (color) | 0.05 |
| 10 | Magnesium Stearate | 0.12 |
| | Trilayer Tablet Core (Third Layer) | |
| 11 | Polyethylene Oxide (Polyox WSR N303) (PEO) | 26.83 |
| 12 | Sodium Chloride | 7.80 |
| 13 | Povidone (PVP) | 3.90 |
| 14 | Magnesium Stearate | 0.49 |
| | Semipermeable Membrane Coat | |
| 15 | Cellulose Acetate | 7.90 |
| 16 | Polyethylene Glycol | 0.88 |
| | Immediate Release Drug Coat | |
| 17 | Selexipag | 0.20 |
| 18 | Hydroxypropylmethyl Cellulose (HPMC) | 2.44 |
| 19 | Polyethylene Glycol (PEG) | 0.78 |

Manufacturing Procedure:
A. Preparation of First Layer and Second Layer Granules
  1. Preparation of Binder Solution: Add PVP in Isopropyl Alcohol (950%) and stir it till get clear solution.
  2. Co-sift Selexipag, PEO and color through appropriate screen. Sift magnesium stearate through appropriate screen.
  3. Transfer the step (2) Selexipag, PEO and color in rapid mixture granulator and mix it for 15 minutes.
  4. Perform granulation of the step (3) material using the step (1) binder solution.
  5. Dry the step (4) wet granules in dryer till desired LOD is achieve.
  6. Sift the step (5) granules through appropriate screen and mill the oversize granules, if any, retain on the screen in appropriate mill using appropriate milling screen.
  7. Blend the step (6) granules with the step (2) magnesium stearate in blender for appropriate time at appropriate blending speed.
B. Preparation of Third Layer Granules
  8. Preparation of Binder Solution: Add PVP in Isopropyl Alcohol (95%) and stir it till get clear solution.
  9. Sift PEO and sodium chloride through appropriate screen. Sift magnesium stearate through appropriate screen.
  10. Transfer the step (9) PEO and sodium chloride in rapid mixture granulator and dry mix it for 10 minutes.
  11. Perform granulation of the step (10) material using the step (8) binder solution.
  12. Dry the step (11) wet granules in dryer.
  13. Sift the step (12) granules through appropriate screen and mill the oversize granules, if any, retain on the screen in appropriate mill using appropriate milling screen.
  14. Blend the step (13) granules with the step (9) magnesium stearate in blender for appropriate time at appropriate blending speed.
C. Trilayer Tablet Preparation
  15. Compress the Trilayer tablet on compression machine with appropriate hardness by first filling the first layer granules followed by the second layer granules followed by third layer granules.
D. Semipermeable Membrane Coating
  16. Preparation of coating solution: Add polyethylene glycol followed by cellulose acetate in mixture of Acetone:Water (99:1) and stir it till get clear solution.

17. Coat the step (15) Trilayer tablet in coater using step (16) coating solution using appropriate coating parameters.

E. Drilling

18. Drill the step (17) tablets on the first layer side (red color layer).

F. Immediate Release Drug Over Coat

19. Preparation of Coating Solution: Add one by one coating components, Selexipag followed by PEG followed by HPMC, in water and stir it for at least 60 minutes.

20. Coat the step (18) tablets in coater using the step (19) coating solution using appropriate coating parameters.

The invention claimed is:

1. A controlled-release pharmaceutical composition comprising a therapeutically effective amount of Selexipag or active metabolite thereof, and one or more pharmaceutically acceptable carriers, wherein the pharmaceutical composition consists of selexipag or active metabolite thereof as a sole pharmaceutical active agent, and a total amount of the pharmaceutically acceptable carriers contained in the controlled-release pharmaceutical composition is not less than about 40% w/w of the total weight of the controlled-release pharmaceutical composition, wherein the at least one pharmaceutically acceptable carrier is a release rate-controlling ingredient, in an amount of not less than about 2.15% w/w of the total weight of the controlled-release pharmaceutical composition, selected from the group consisting of cellulose acetate, cellulose acetate butyrate, cellulose triacetate, ethyl cellulose, polymethacrylate and its copolymer, polyvinyl acetate, copolymers of vinyl pyrrolidone and vinyl acetate, xanthan gum, acacia gum, diutan gum, tragacanth, gellan gum, guar gum, fenugreek gum, locust bean gum, pullulan, welan gum, wax, hydroxyethyl cellulose, hydroxypropylmethyl cellulose, hydroxypropyl cellulose, polyethylene oxide, and polyvinylpyrrolidone, wherein the controlled-release pharmaceutical composition is devoid of a pH-sensitive polymer coat that is substantially insoluble at a pH of <5 but soluble in water at a pH of >5, and it releases, when measured using USP apparatus 2 at 50 or 150 RPM in 900 ml of an aqueous medium having pH of 6.8±0.5 and a temperature of 37°+1° C., the selexipag or active metabolite thereof in an amount of less than about 50% of the total weight of the Selexipag or active metabolite thereof contained in the pharmaceutical composition over 45 minutes, thereby a mean or median Tmax attained after administration of the dosage form to a mammal in fasting condition is at least greater than 2 hours for the Selexipag and/or at least greater than 5 hours for the active metabolite of Selexipag, thereby the controlled release pharmaceutical composition reduces incidence of at least one side effect associated with the Selexipag, or active metabolite thereof, compared to the immediate-release dosage form comprising the same amount of Selexipag or active metabolite thereof.

2. The controlled-release pharmaceutical composition of claim 1, wherein the therapeutically effective amount of the Selexipag or active metabolite thereof is at least 0.2 mg.

3. The controlled-release pharmaceutical composition of claim 1 is formulated as a matrix system, wherein the matrix system is formulated in the form of a tablet, or multiparticulate, and the Selexipag or active metabolite thereof is embedded within a matrix of the one or more release rate controlling ingredients, wherein the matrix optionally further comprising the one or more pharmaceutically acceptable additives selected from the group of filler, diluent, disintegrant, anti-tacking agent, binder, glidant, surfactant, wetting agent, lubricant, anti-oxidant, plasticizer, sweetener, coloring agent, sugar, salt, acid, and osmotic agent.

4. The controlled-release pharmaceutical composition of claim 3, wherein a full or portion of the outside surface of the matrix system is covered with a membrane of the release-rate controlling ingredient.

5. The controlled-release pharmaceutical composition of claim 1 is formulated as a reservoir system, wherein the reservoir system is formulated in the form of a tablet, or multiparticulate, and is comprised of:

a. at least one inert core consisting of the Selexipag or active metabolite thereof, and optionally, at least one pharmaceutically acceptable additive selected from the group of filler, diluent, disintegrant, anti-tacking agent, binder, glidant, surfactant, wetting agent, lubricant, antioxidant, plasticizer, sweetener, coloring agent, sugar, salt, acid, and osmotic agent; and b. a coat surrounding the at least one inert core, wherein the coat comprising the one or more release rate controlling ingredients.

6. The controlled-release pharmaceutical composition of claim 5, optionally, is further comprised of a coat of pH-sensitive polymer surrounding the reservoir system, wherein the pH-sensitive polymer is substantially insoluble at pH<5.0.

7. The controlled-release pharmaceutical composition of claim 1, wherein at least another pharmaceutically acceptable carrier is at least one selected from the group of filler, disintegrant, anti-tacking agent, binder, glidant, surfactant, wetting agent, lubricant, plasticizer, sweetener, colouring agent, sugar, salt, acid, and osmotic agent.

* * * * *